US00PP17486P3

(12) United States Plant Patent
Gossett

(10) Patent No.: US PP17,486 P3
(45) Date of Patent: Mar. 13, 2007

(54) ***TIARELLA* PLANT NAMED 'MORNING STAR'**

(50) Latin Name: ***Tiarella* hybrid**
Varietal Denomination: Morning Star

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 79 days.

(21) Appl. No.: 11/155,224

(22) Filed: Jun. 16, 2005

(65) Prior Publication Data

US 2006/0288460 P1 Dec. 21, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct cultivar of *Tiarella* plant characterized its compact habit with numerous flowering stems and pink flowers, distinct leaf form and coloration.

1 Drawing Sheet

Botanical denomination: *Tiarella* hybrid.
Variety designation: 'Morning Star'.

BACKGROUND OF THE INVENTION

The present invention relates to a new and distinct cultivar of a hardy herbaceous perennial of the genus *Tiarella,* and known by the cultivar name 'Morning Star'. The genus *Tiarella* is a member of the family Saxifragaceae.

The new cultivar originated as a cross between unknown parents. This new *Tiarella* was one of many seedlings grown from select, proprietary, interspecific hybrids that were unnamed, experimental varieties that were mass pollinated in the greenhouse in Canby, Oreg. The instant plant was selected as outstanding from the above seedlings. From observation of the characteristics exhibited by the instant plant, it is an interspecific hybrid. As such no species designations are given.

SUMMARY OF THE INVENTION

This plant is characterized by the following:

1. Compact habit.
2. Numerous flowering stems.
3. Attractive maple shaped leaf with dark pattern along main veins.
4. Pink buds and white flower color.
5. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a one-and a half year old *Tiarella* 'Morning Star' in bloom in the garden in late May in Canby, Oreg.

DETAILED PLANT DESCRIPTION

The following is a detailed description of the new *Tiarella* hybrid based on observations of two-year-old plants grown in the garden, in the ground, in shade, under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical name: *Tiarella* hybrid.
Cultivar name: 'Morning Star'.
Plant:
- *Type.*—Herbaceous perennial.
- *Hardiness.*—USDA Zones 4 to 9.
- *Form.*—Basal clump.
- *Size.*—35 cm wide and 17 cm high.
- *Vigor.*—Excellent.
- *Roots.*—Fibrous, freely branching, fine, and white in color, White 155A. Roots develop easily from divisions.

Foliage:
- *Type.*—Simple.
- *Arrangement.*—Rosette.
- *Shape.*—Ovate to orbicular in outline.
- *Lobing.*—Deeply 7 parted with terminal lobe the longest and prominent open spaces between the lobes and with each lobe irregularly lobed again. Terminal 3 lobes narrow at base making the leaf distinct.

*Margins.*—Crenate.
*Venation.*—Palmate.
*Apex.*—Mucronulate.
*Base.*—Cordate and usually overlapping.
*Blade length.*—Variable, 8 to 10 cm.
*Blade width.*—Variable, 5.5 to 9.5 cm.
*Surface texture.*—Hirsute top and bottom.
*Petiole length.*—Variable, 17 to 18 cm.
*Petiole texture.*—Strongly pubescent.
*Petiole color.*—Brown 200A overall.
*Leaf color.*—From Yellow Green 146A in spring to Yellow Green 147A in summer with Brown 200B along main veins and outwards covering one-third of the leaf blade. In winter the leaves stay Yellow Green 147A and the pattern covers half or more of the leaf, Brown 200A. Bottom side is Yellow Green 148B.

Inflorescence:
*Type.*—Raceme.
*Number of raceme in first spring flush.*—160.
*Flower number.*—60 per raceme, above branching.
*Bloom period.*—April to May with sporadic rebloom throughout the summer and fall.
*Peduncle.*—With 0 to 1 leaf bract and branching 1 to 5 times, each branch with 5 to 15 flowers, branches held close to main flowering stem and 2 to 13 cm long. Height — 30 to 34 cm. Width — 2 mm at the widest point. Color — Greyed Green 197A near top and Greyed Purple 187A near base. Texture — Hispid.
*Pedicel.*—Length — 0.4 to 0.5 cm. Texture — Puberulent. Color — Red Purple 72A.

Flower bud:
*Size.*—0.4 cm deep and 0.3 cm wide.
*Description.*—Ovoid, downfacing until open.
*Color*—Pink, Greyed Purple 186C.

Flower:
*Type.*—Perfect, actinomorphic, sepals petaloid.
*Shape.*—Rotate.
*Petal and sepal number.*—5 petals, 5 fused sepals.
*Flower size.*—0.7 wide and 0.5 cm. deep including stamens.
*Petal shape.*—Lanceolate with a clawed base, margins entire, apex acute.
*Petal size.*—0.6 cm long and 0.1 cm. wide.
*Petal color.*—White 155A on both sides.
*Calyx.*—Petaloid, parted almost to the base, lobes lanceolate, tips acute, margins entire.
*Calyx size.*—1.1 cm wide and 0.4 cm deep.
*Calyx color.*—Greyed Purple 186D on lobes to White 155A at base on inner surface and Greyed Purple 186D on the outside.
*Stamens.*—10, conspicuously exerted.
*Filaments.*—White 155A, 0.3 cm long.
*Anthers undehisced.*—Orange 28C.
*Pollen color.*—Orange 28B.
*Pistil.*—White 155A.
*Fragrance.*—Slight.

Fruit:
*Type.*—A one-celled capsule, beak-like, composed of two unequal parts.
*Size.*—0.7 cm long.
*Color.*—Brown 200C.

Seeds:
*Color.*—Black 202A.
*Shape.*—Minute, oval, 1 mm long.
*Fertility.*—Fertile.

Disease and pest tolerance: This new hybrid shows good mildew tolerance, the main problem for *Tiarella.* All *Tiarella* are susceptible to root weevils.

COMPARISONS WITH SIMILAR *TIARELLA*

Compared with *Tiarella* 'Ninja' (U.S. Plant Pat. No. 11,168), *Tiarella* 'Morning Star' has similar leaf shape and size, but the lobes are more deeply cut and narrower. The plant is more compact, with much better flower number and flower stem number.

I claim:

1. A new and distinct cultivar of *Tiarella* plant substantially as illustrated and described.

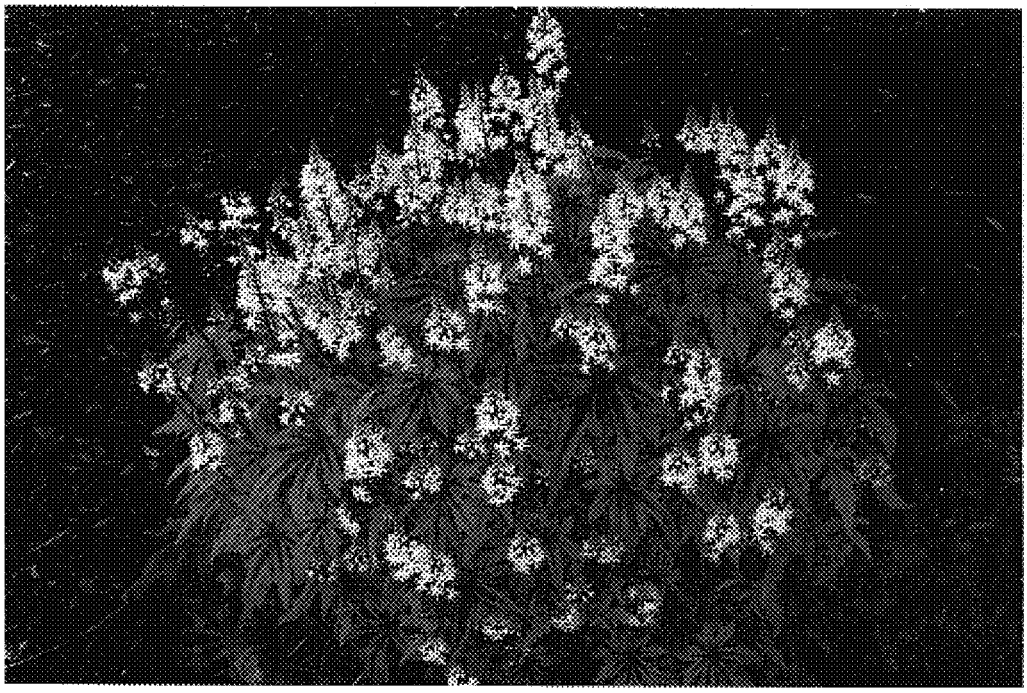

* * * * *